(12) United States Patent
Schrod et al.

(10) Patent No.: US 9,550,707 B2
(45) Date of Patent: Jan. 24, 2017

(54) PROCESS FOR PRODUCTION OF HYDROCARBON CHEMICALS FROM CRUDE OIL

(71) Applicant: Saudi Basic Industries Corporation, Riyadh (SA)

(72) Inventors: Heinrich Manfred Schrod, Riyadh (SA); Wilfried J. Petzny, Kempten (DE)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 372 days.

(21) Appl. No.: 13/856,065

(22) Filed: Apr. 3, 2013

(65) Prior Publication Data

US 2013/0267745 A1 Oct. 10, 2013

Related U.S. Application Data

(60) Provisional application No. 61/619,994, filed on Apr. 4, 2012.

(51) Int. Cl.
*C10G 51/00* (2006.01)
*C07C 4/04* (2006.01)
(Continued)

(52) U.S. Cl.
CPC ............... *C07C 4/04* (2013.01); *C10B 55/00* (2013.01); *C10B 57/045* (2013.01); *C10G 7/06* (2013.01);
(Continued)

(58) Field of Classification Search
CPC ............. C07C 4/04; C10G 9/36; C10G 57/00; C10G 9/005; C10G 51/023; C10G 51/06; C10G 51/00; C10G 69/00; C10G 7/06; C10B 57/045; C10B 55/00
See application file for complete search history.

(56) References Cited

U.S. PATENT DOCUMENTS 2,906,694 A 9/1959 Dunlap et al.
3,671,419 A 6/1972 Ireland et al.
(Continued)

FOREIGN PATENT DOCUMENTS

| WO | 9626992 A1 | 9/1996 |
| WO | 2008051334 A2 | 5/2008 |
| WO | 2012005861 A1 | 1/2012 |

OTHER PUBLICATIONS

International Search Report; International Application No. PCT/IB2013/052668; International Filing Date: Apr. 3, 2013; Date of Mailing: Dec. 2, 2013; 7 Pages.
(Continued)

*Primary Examiner* — Randy Boyer
*Assistant Examiner* — Juan Valencia
(74) *Attorney, Agent, or Firm* — Cantor Colburn LLP

(57) ABSTRACT

An integrated process comprising to convert crude oil, comprising: converting crude oil (10) in a feed preparation facility (800) by separating the crude oil to a gas fraction (101), liquid fraction (102), and first residuum fraction in an atmospheric distillation unit (100); separating the 1$^{st}$ residuum to a vacuum gas oil fraction (202) and a second residuum (201) in a vacuum distillation unit (200); converting the vacuum gas oil fraction to a CU gas fraction (301,401), a CU liquid fraction (302), and an CU higher boiling fraction (303,402) in a cracking unit (300,400); and processing the second residuum fraction to DCU gas oil/lighter fraction (501) in a coking unit (500); and steam cracking at least one of the gas fraction (101), liquid fraction
(Continued)

(102), CU gas fraction (301,401), and DCU gas oil/lighter fraction (501) to the hydrocarbon products (920).

12 Claims, 5 Drawing Sheets

(51) Int. Cl.
| | |
|---|---|
| C10B 55/00 | (2006.01) |
| C10G 7/06 | (2006.01) |
| C10G 69/00 | (2006.01) |
| C10B 57/04 | (2006.01) |
| C10G 51/02 | (2006.01) |
| C10G 51/06 | (2006.01) |
| C10G 9/00 | (2006.01) |
| C10G 57/00 | (2006.01) |
| C10G 9/36 | (2006.01) |

(52) U.S. Cl.
CPC ............... *C10G 9/005* (2013.01); *C10G 9/36* (2013.01); *C10G 51/00* (2013.01); *C10G 51/023* (2013.01); *C10G 51/06* (2013.01); *C10G 57/00* (2013.01); *C10G 69/00* (2013.01)

(56) References Cited

U.S. PATENT DOCUMENTS

| | | | |
|---|---|---|---|
| 3,702,292 A * | 11/1972 | Burich | 208/80 |
| 3,901,667 A | 8/1975 | Herrmann | |
| 4,411,769 A | 10/1983 | Oldweiler | |
| 2008/0210597 A1* | 9/2008 | Yoo et al. | 208/41 |
| 2010/0329935 A1 | 12/2010 | McGehee et al. | |
| 2011/0042269 A1* | 2/2011 | Kuechler | C10G 9/38 |
| | | | 208/57 |

OTHER PUBLICATIONS

Written Opinion of the International Searching Authority; International Application No. PCT/IB2013/052668; International Filing Date: Apr. 3, 2013; Date of Mailing: Dec. 2, 2013; 10 Pages.

* cited by examiner

PROCESS FOR PRODUCTION OF HYDROCARBON CHEMICALS FROM CRUDE OIL

BACKGROUND

Field of the Invention

This invention is related to a process and system for converting crude oil into improved feedstock for steam cracking to produce chemical hydrocarbons and for a process and system for integrating a steam cracking feedstock preparation process with a steam cracking facility. More specifically this process can include process subsequences including an atmospheric distillation unit(s), vacuum distillation unit(s), cracking unit(s) and coking unit(s), all operated at conditions to produce feed materials for steam cracking superior to those generated in typical refinery operations.

Background

Conventional petroleum refinery configurations, selection and arrangement of processing units, are designed to provide optimum transportation fuels, not chemical feedstocks. Light products tend to be minimized as of lower economic value. Naphtha, for example, is usually converted by catalytic reformer to highly aromatic and branched paraffins useful as high octane transportation fuel. However, naphtha is also a valued source of chemical feedstock as it can be easily converted to olefins and aromatic by steam cracking. In general, therefore, petroleum refineries have not been configured to maximize chemical feedstocks. The present invention is a process configuration that minimizes conventional transportation fuel production and maximizes chemical feedstock and chemical-grade light olefins and aromatics (for example, ethylene, propylene, $C_4$ mono-olefins, butadiene, benzene, toluene, xylene, ethylbenzene and styrene).

Before 2005 the price of crude ranged from about $15-$40/bbl and the price and availability of naphtha such that the differential value was about $30-$50/bbl. As a result it was not generally economic to upgrade crude oil to naphtha (and other steam cracker feeds). More recently the differential value of crude and naphtha has increased to $100-$200/bbl making the purchase of naphtha as a sole source of steam cracking (chemical feedstock production) far less attractive. Thus, intentional conversion of crude oil solely to steam cracker feedstock has become desirable. Providing special configurations of refining units to produce only chemical feedstocks is unique and not previously considered. Such configurations require careful selection and operation of conventional refining processes to produce unexpected results and economies.

There continues to be a need for more efficient processes and systems to convert crude oil to chemical feedstocks.

SUMMARY OF THE INVENTION

In broad aspect the process of the invention is an integrated process configuration based on the strategic selection of conventional oil refining units, such as atmospheric distillation, vacuum distillation, fluid catalytic cracking, hydrocracking, coking and hydrotreating, to convert substantially all of a crude oil feed stream into fractions suitable for conversion to chemical. The process will produce over 50% conversion and preferably over 60% of crude oil to steam cracking suitable feedstocks including, inter alia, aliphatic gases, naphtha, and gas oil.

In another aspect, the process is the integration of the above described configuration of refining units with a steam cracking facility to achieve synergetic benefits and the overall conversion of crude oil to olefins and aromatic compounds suitable for chemical production.

More specific aspects include the selection of individual refining units in specified sequences to maximize the efficient conversion of crude oil to chemicals.

DETAILED DESCRIPTION

Figure 1:
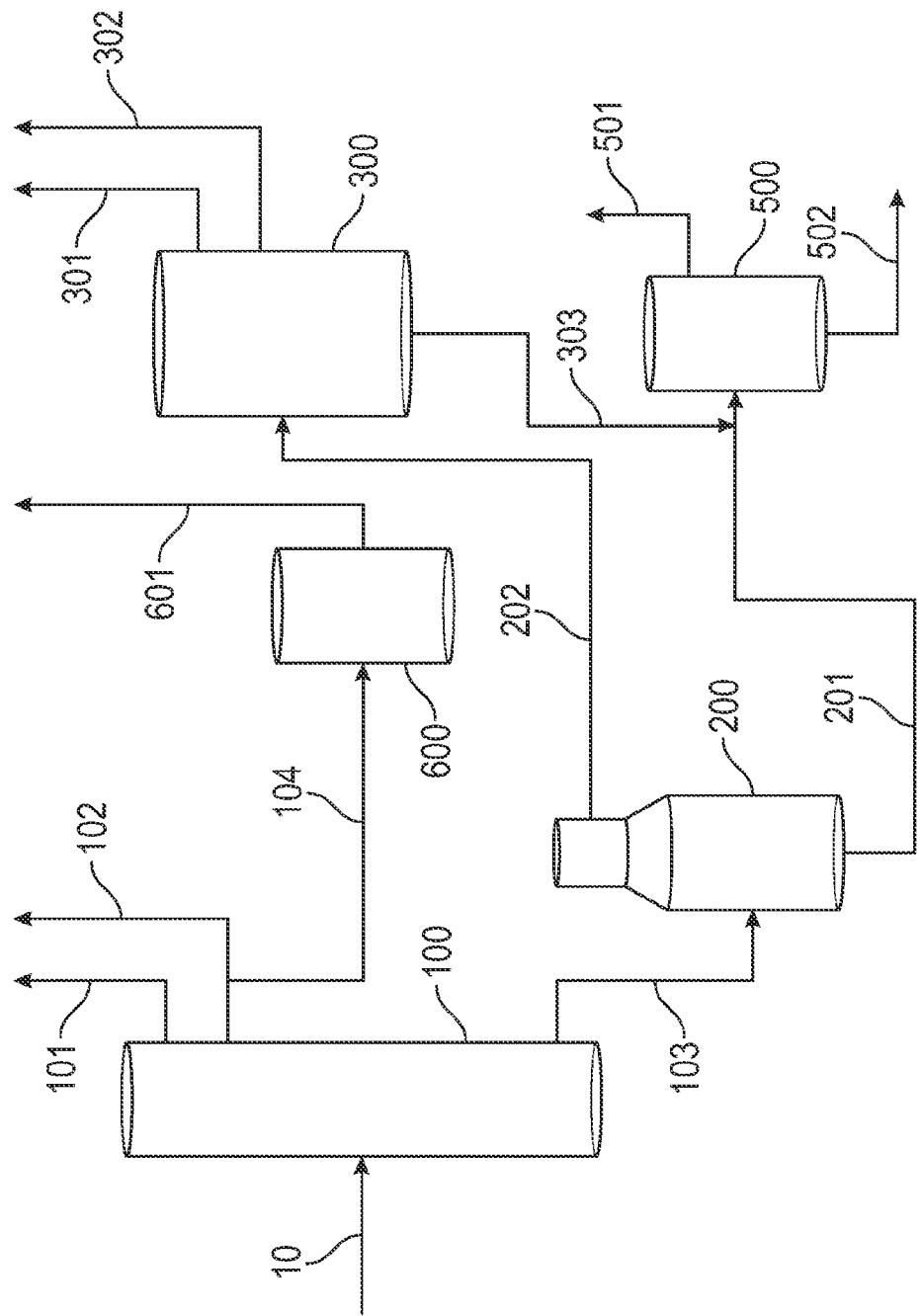
FIG. 1 is a schematic flow diagram showing major components of an embodiment of the invention.

The present invention provides an integrated process configuration in a crude oil processing plant solely dedicated to production of steam cracker feedstock (a feed preparation facility—"FPF") and also a feed preparation facility specially integrated with an associated steam cracking facility. Thus, there is provided an integrated process that minimizes the amount of crude oil needed for maximum value of chemical feedstock products, provides better quality steam cracking feedstock and provides important synergies between a FPF and steam cracker. By integration the light olefins get a "free ride" in the steam cracker separation unit, methane from the FPF is used for heating in the steam cracker unit and $C_3$ and $C_4$ paraffins, naphtha and gas oil produced provide excellent feedstock for the steam cracker. Hydrogen produced in the steam cracker can supply as much as half the hydrogen need in the FPF. This hydrogen availability allows more extensive hydrogenation of the steam cracking feedstock produced in the FPF and enhances its value. In some embodiments pyrolysis fuel oil produced in the steam cracker (that would otherwise be used as fuel) is recycled to the FPF to replace the amount of crude oil feed needed.

In broad aspect, this invention is an integrated process for converting crude oil into petroleum fractions including suitable lower boiling fractions from conversion processes especially suitable for processing in a steam cracking facility for the production of olefins and aromatic compounds useful for chemical production and the integration of the process with a steam cracking facility to produce hydrocarbon chemicals including olefins (e.g., polymer grade light olefins).

In a specific embodiment of a process of the invention crude oil is first processed in an atmospheric distillation unit to separate gas oil and lighter fractions from higher boiling components (atmospheric residuum "resid"), which are passed to a vacuum distillation unit where it is separated into a gas oil fraction and vacuum residue fraction, the vacuum gas oil and the residue fractions are then passed to a "cracking" unit or units to produce fractions suitable for steam cracking and higher boiling and/or a solid fraction that are passed to a delayed coking unit in which gas oil and lighter fractions and coke are produced, the lighter fraction being separated and useful for steam cracking feedstock. In one aspect the "cracking" unit is a fluid catalytic cracking unit, in another a hydrocracking unit and in still another both a fluid catalytic cracker and a hydrocracking unit, each processing different fractions of the vacuum distillation unit.

"Steam cracking" and steam cracking facility, as the terms are used herein, is a petrochemical process in which saturated hydrocarbons are broken down into smaller, often unsaturated, hydrocarbons such as ethylene and propylene. In steam cracking hydrocarbon feeds like gas oil, naphtha, liquid petroleum gas (LPG) or ethane is diluted with steam and briefly heated in a furnace without the presence of oxygen. Typically, the reaction temperature is very high, at around 850° C., but the reaction is only allowed to take place very briefly, usually with residence times of milliseconds. After the cracking temperature has been reached, the gas is quickly quenched to stop the reaction in a transfer line heat exchanger or inside a quenching header using quench oil. The products produced in the reaction depend on the composition of the feed, the hydrocarbon to steam ratio and on the cracking temperature and furnace residence time. Light hydrocarbon feeds such as ethane, LPGs or light naphtha give product streams rich in the lighter polymer grade olefins, including ethylene, propylene, and butadiene. Heavier hydrocarbon (full range and heavy naphtha and gas oil fractions) also give products rich in aromatic hydrocarbons. The process also results in the slow deposition of coke, a form of carbon, on the reactor walls. Decoking requires the furnace to be isolated from the process and then a flow of steam or a steam/air mixture is passed through the furnace coils. This converts the hard solid carbon layer to carbon monoxide and carbon dioxide. Once this reaction is complete, the furnace is returned to service. "Facility" means the steam cracking unit and all its associated accessory process units.

"Cracking" as the term is used herein and in the claims means technology for breaking heavier petroleum fractions into lower boiling fractions and includes both fluid catalytic cracking and hydrocracking.

"Fluid catalytic cracking" and fluid catalytic unit ("FCCU") as those terms are used herein are commonly used processes in all modern oil refineries. Cracking takes place generally using a very active zeolite-based catalyst in a short-contact time vertical or upward-sloped pipe called the "riser". Pre-heated feed is sprayed into the base of the riser via feed nozzles where it contacts extremely hot fluidized catalyst at 1230° F. to 1400° F. (665° C. to 760° C.). The hot catalyst vaporizes the feed and catalyzes the cracking reactions that break down the high-molecular weight oil into lighter components including LPG, gasoline, and diesel. The catalyst-hydrocarbon mixture flows upward through the riser for just a few seconds, and then the mixture is separated via cyclones. The catalyst-free hydrocarbons are routed to a main fractionator (a component of the FCCU for separation into fuel gas, LPG, gasoline, naphtha, light cycle oils and heavy fuel oil). "Spent" catalyst is disengaged from the cracked hydrocarbon vapors and sent to a stripper where it is contacted with steam to remove hydrocarbons remaining in the catalyst pores. The "spent" catalyst then flows into a fluidized-bed regenerator where air (or in some cases air plus oxygen) is used to burn off the coke to restore catalyst activity and also provide the necessary heat for the next reaction cycle, cracking being an endothermic reaction. The "regenerated" catalyst then flows to the base of the riser, repeating the cycle.

"Hydrocracking" as the term is used herein is a catalytic cracking process assisted by the presence of an elevated partial pressure of hydrogen gas. Similar to a hydrotreating, the function of hydrogen is the purification of the hydrocarbon stream from sulfur and nitrogen hetero-atoms. The products of this process are saturated hydrocarbons; depending on the reaction conditions (temperature, pressure, and catalyst activity) these products range from ethane, LPG to heavier hydrocarbons consisting mostly of isoparaffins. Hydrocracking is normally facilitated by a bifunctional catalyst that is capable of rearranging and breaking hydrocarbon chains as well as adding hydrogen to aromatics and olefins to produce naphthenes and alkanes. Major products from hydrocracking are kerosene boiling range fractions, gasoline boiling range fractions and LPG. All these products have a very low content of sulfur and other contaminants and generally will not need to be further hydrotreated for use as a steam cracking feedstock.

A coker or "coking unit" is an oil refinery processing unit that converts residual oil into low molecular weight hydrocarbon gases, naphtha, light and heavy gas oils, and petroleum coke. The process thermally cracks the long chain hydrocarbon molecules in the residual oil feed into shorter chain molecules. Commercially available technologies include a delayed coker, a fluid coker, a Flexicoker™, a visbreaker or a catalytic hydrovisbreaker, but a delayed coker is generally preferred.

In this specification several petroleum fractions are referred to, such as naphtha, gas oil and the like. While there is no commonly understood fixed boiling range for these fractions the following is an approximation of appropriate boiling ranges: straight run gasoline or light naphtha-90-190° F. (32-88° C.); naphtha or heavy naphtha-190-380° F. (88-193° C.); kerosene-380-520° F. (193-271° C.); atmospheric gas oil-520-650° F. (271-343° C.); atmospheric residuum—650° F.+(343  C+); vacuum gas oil-650-1,000° F. (343-538° C.); and vacuum residuum 1,000° F.+(538° C.+).

The steam cracking facility liquid feedstocks produced by the process of the invention are processed in a hydrotreating unit(s), if necessary, to remove sulfur compounds and other contaminates. Hydrotreating is a well known process to those skilled in the art and it is well within the skill in the art to determine if hydrotreating of a hydrocarbon product is needed before it is suitable for steam cracking.

There are, at least, six (6) specific embodiments of the present invention within the broad scope of the steam cracking feed preparation aspect of the invention as summarized in the following Table 1.

TABLE 1

| Embodiment | Catalytic Reformer*** | Pyrolysis fuel oil Recycle | Refining Process Units |
|---|---|---|---|
| I | Yes | No | 100% FCCU* |
| II |  | No | 100% FCCU |
| III |  | No | 50% FCCU; 50% HCU** |
| IV |  | Yes | 100% FCCU |
| V |  | Yes | 50% FCCU; 50% HCU |
| VI |  | Yes | 100% HCU |

*Fluid catalytic cracking unit:
**Hydrocracking unit:
***Catalytic reforming unit The fluid catalytic cracking unit, hydrocracking unit and catalytic reforming unit and hydrotreating units may be any of the commercially available designs. The hydrocracking unit may be, for example, a VisBreaker™ a hydrocracking technology licensed by Foster Wheeler Corp., UOP, Chevron and Shell.

Suitable fluid catalytic cracking units may, but are not limited to, those based on technology available for license from UOP and KBR Orthoflow.

A useful summary of the features of each of these processing technologies may be found in the 2004 and 2010 Refining Process issue of Hydrocarbon Processing available from Gulf Publishing Company and online at by searching for RefiningProcesses_2004.pdf or later editions.

Any crude oil is suitable as the source material for the process of this invention, including Arabian Heavy, Arabian Light, other Gulf crudes, Brent, North Sea crudes, North and West African crudes, Indonesian and Chinese crudes.

In another aspect the invention is an integrated facility in which a feed preparation facility (FPF) as described above is strategically connected to an associated steam cracking facility on a single site. This configuration maximizes the conversion of crude oil to chemical and polymer grade hydrocarbons (from the steam cracking unit or units) and results in significant economic synergies and cost savings as are discussed further below.

Embodiments of the invention may be better understood by reference to the drawings.

Specific Embodiment I is illustrated in FIG. 1. Embodiment I is a feed preparation facility which comprises a crude oil atmospheric distillation unit, 100, a vacuum distillation unit, 200, a fluid catalytic cracking unit, 300, a catalytic reforming unit, 600 and a delayed coking unit, 500. Crude oil enters the processing sequence at 10 into atmospheric distillation column 100 where the crude oil is separated into gas fractions, 101, liquid fractions 102 (fractions boiling at and below the boiling range of gas oil, including straight run gasoline, naphtha and gas oil) and a first residuum fraction 103. A portion of the liquid fraction in the naphtha and gasoline boiling range passes to the catalytic reforming unit 600 where much of the feed is converted to naphthalene and aromatic compounds. The aromatics, benzene, toluene and xylene (BTX), may be separated before the stream, 601, is sent to the steam cracking or may remain with the stream passed to the steam cracking unit and be separated from the steam cracking products together with any other BTX produced. The atmospheric distillation residuum fraction passes to a vacuum distillation unit 200 where the feed is again separated into a second residuum fraction 201 and a lighter vacuum gas oil fraction 202. The vacuum gas oil fraction is passed to a fluid catalytic cracking unit, 300 where the feed is converted to products suitable for steam cracking. Heavy cycle oil (and optionally other high boiling fractions) 303 from the fluid cracking unit 300 passes to the coking unit 500. The vacuum distillation unit residuum fraction is passed to a coking unit (preferable a delayed Coker or Flexi-Coker™). In the coking unit, gas oil and lighter fraction are produced and pass out via conduit 501 and coke is removed via conduit 502. Most of the metals and ash contained in the crude oil end up in this coke fraction.

Figure 2:
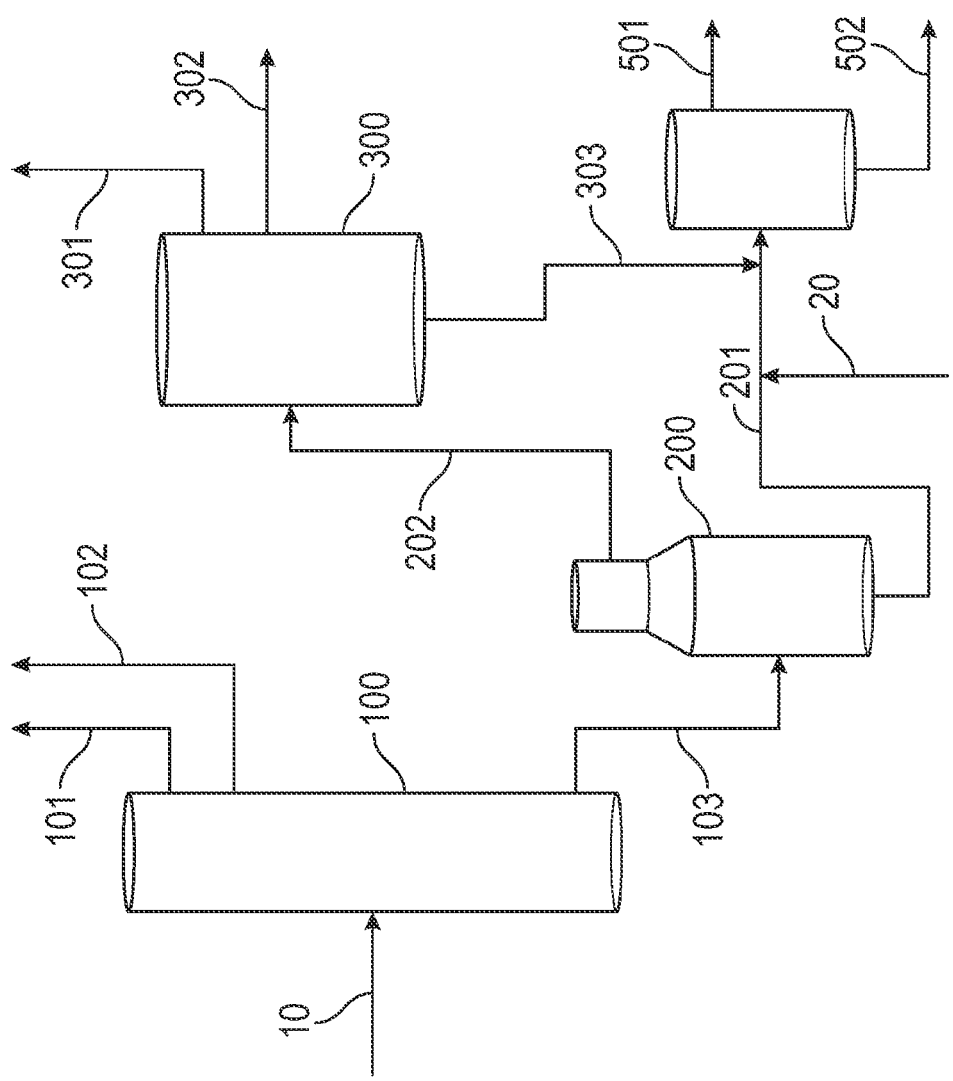
FIG. 2 is a schematic flow diagram showing major components of an embodiment of the invention.

Embodiments II and IV, are illustrated in FIG. 2, the difference between the two being that in Embodiment II there is no recycle of pyrolysis fuel oil, 20, from an associated steam cracking unit(s), whereas in Embodiment IV substantially all of the pyrolysis fuel oil generated in the associated steam cracking unit(s) is recycled to the feed preparation process where it enters the process via conduit 20 to mix with the vacuum residue from vacuum distillation unit, 200.

Embodiments II and IV comprise a crude oil atmospheric distillation unit, 100, a vacuum distillation unit, 200, a fluid catalytic cracking unit, 300 and a delayed coking unit, 500. Crude oil entering the processing sequence at 10 into atmospheric distillation column 100 where the crude oil is separated into gas fractions, 101, liquid fraction 102 (fractions boiling at and below the boiling range of gas oil) and a residuum fraction 103. The residuum fraction, 103, passed to a vacuum distillation unit 200 where the feed is again separated into a second residuum fraction 201 and a vacuum gas oil fraction 202. The vacuum gas oil fraction is passes to a fluid catalytic cracking unit, 300, where it is converted to products suitable for steam cracking. Heavy cycle oil 303 from the fluid cracking unit 300 passes to the coking unit 500. Gases, 301, and liquid fractions 302 are suitable for steam cracking. The residuum fraction, 201 is passed to a coking unit (preferable a delayed Coker or Flexi-Coker™). In the coking unit, gas oil and lighter fraction are produced and pass out via conduit 501 as feedstock for steam cracking and coke is removed via conduit 502. In Embodiment IV pyrolysis fuel oil produced in an associated steam cracking unit or unit(s) are recycled and enter the process via conduit 20 as additional feed to the coking unit.

Figure 3:
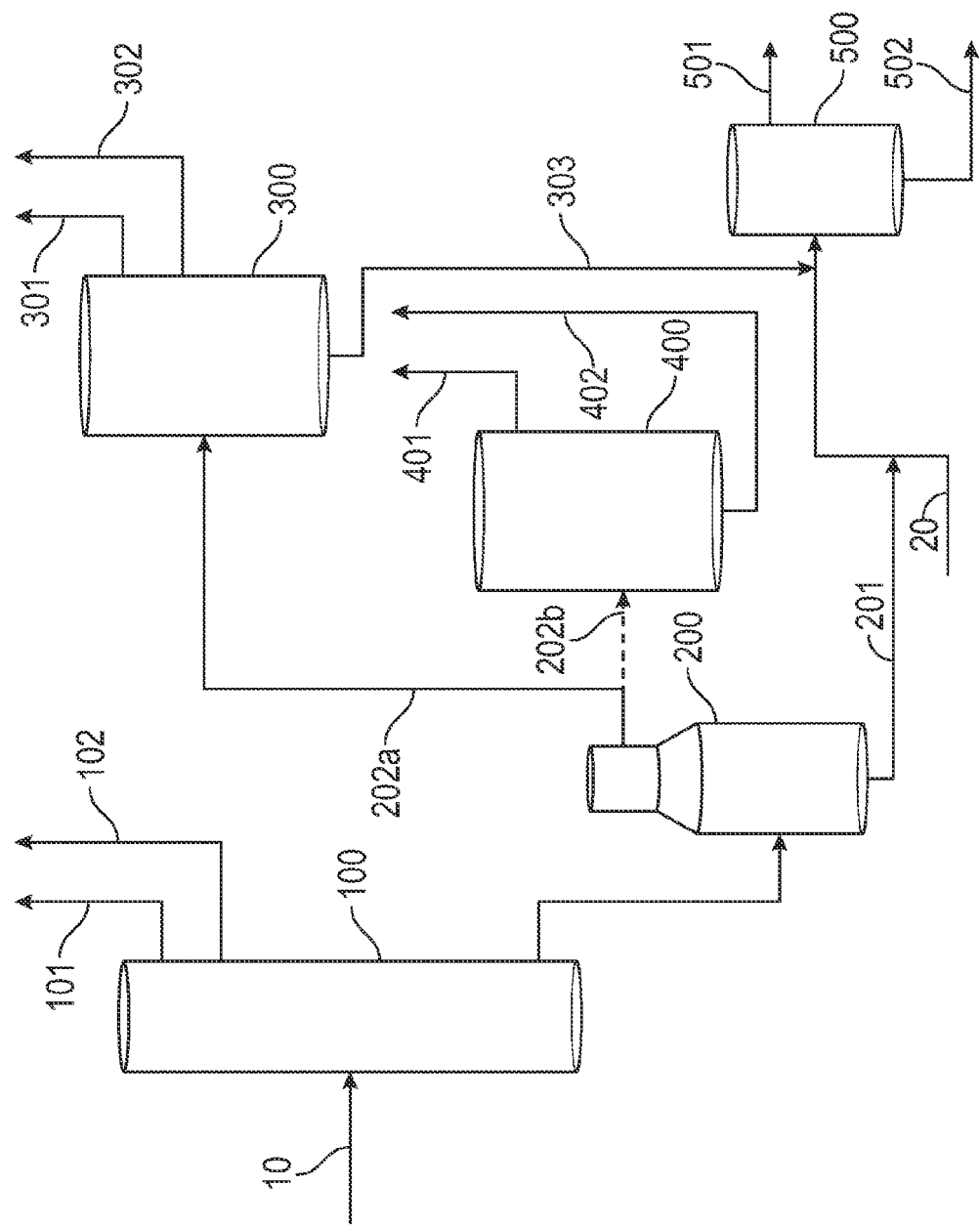
FIG. 3 is a schematic flow diagram showing major components of an embodiment of the invention.

FIG. 3 illustrated the flow scheme of Embodiments III and V. The principal difference in these embodiments and Embodiments II and IV is the addition of a hydrocracking unit ("HCU"), 400, between the vacuum distillation unit, 200, and the coking unit, 500. Vacuum distillation residuum passes via 201 to the coking unit, 500. Vacuum distillate is passed (e.g., 50%) (202a) to a fluid cracking unit and 202b (e.g., 50%) to a hydrocracking unit 400, where gas oil and lighter fractions are produced, 401, and the heavier boiling residue, 402, is also suitable as steam cracking feed. Thus streams 101, 102, 301, 302, 401, and 402 can serve as steam cracking feedstock. In Embodiment V pyrolysis fuel oil produced in an associated steam cracking unit(s) are recycled and enter the process via conduit 20 as additional feed to the coking unit.

Figure 4:
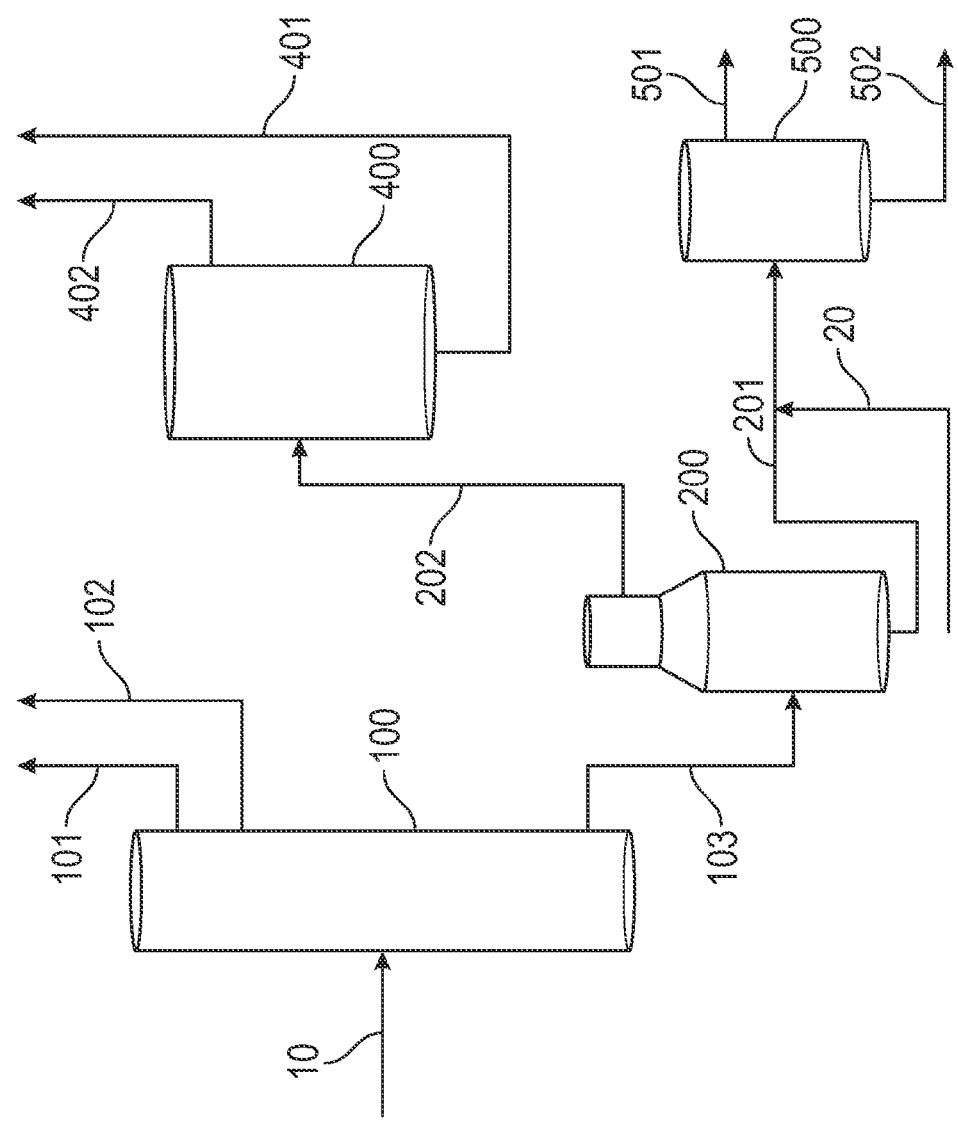
FIG. 4 is a schematic flow diagram showing major components of an embodiment of the invention.

Embodiment VI is illustrated in FIG. 4. Embodiment VI comprises a crude oil atmospheric distillation unit, 100, a vacuum distillation unit, 200, and a delayed coking unit, 500. Crude oil entering the processing sequence at 10 into atmospheric distillation column 100 where the crude oil is separated into gas fractions, 101, liquid fraction 102 (fractions boiling at and below the boiling range of gas oil) and a residuum fraction 103. The residuum fraction passed to a vacuum distillation unit 200 where the feed is again separated into a second residuum fraction 201 and a vacuum gas oil fraction 202. The vacuum gas oil 202 is passed to a hydrocracking unit 400, where both lighter product (also referred to as gas oil fraction) 402 and heavier product (also referred to as heavier boiling residue) 401 are suitable as steam cracker facility feedstock. In the coking unit, (preferable a delayed Coker or Flexi-Coker™) gas oil and lighter fraction are produced and pass out via conduit 501 and coke is removed via conduit 502. As in Embodiments II and V streams 101, 102, 401, and 402 serve as steam cracking feedstock.

Each of the processing units are operated at conditions typical for such units, which conditions are adjusted to maximize, within the capability of the unit's design, the desired products—i.e. those fraction and products most suitable for steam cracking feedstock. These operating conditions are well known in the art and within the capabilities of those skilled in the art.

The following Table 2 illustrated the different crude requirements, conversion and product production amounts that will be expected from a nominal 40 million metric ton per day processing scheme using Arabian heavy crude.

TABLE 2

|  | Embodiment | | | | | |
| --- | --- | --- | --- | --- | --- | --- |
|  | I | II | III | IV | V | VI |
| Crude oil Required* | 42.8 | 42.0 | 42.2 | 38.1 | 38.0 | 38.0 |
| Naphtha produced | 12.6 | 12.6 | 11.6 | 12.4 | 11.2 | 10.0 |
| Gas Oil Produced | 22.2 | 21.8 | 24.1 | 22.5 | 24.6 | 26.7 |
| Input to FCCU(300) | 9.3 | 9.1 | 4.6 | 8.3 | 4.1 | 0 |
| Input to HCU(400) | 0 | 0 | 4.6 | 0 | 4.1 | 8.3 |
| Input to Coker (500) | 10.9 | 10.7 | 10.3 | 15.0 | 15.0 | 14.9 |
| Recycle Pyrolysis GO(20) | 0 | 0 | 0 | 5.3 | 5.7 | 6.0 |
| Conversion FPU** | 87% | 88% | 89% | 86% | 87% | 87% |
| Conversion FPU + Stm Ckr | 63% | 64% | 64% | 71% | 71% | 71% |

*Million Metric tons;
**Feed Preparation Facility - crude processing scheme

As can be seen, excellent conversion of crude oil of 87-88% can be expected with as much as 71% of the crude oil resulting in high value chemical feedstocks.

Conversions will vary with operating conditions and the nature of the crude oil feed but it is expected to obtain conversions in the steam cracking feed preparation facility of at least 80% and maybe as much as 90%. Overall total conversion of crude oil to chemical hydrocarbon feedstocks of at least 50% and may be 60 to 70%. Thus, there is provides an economic source of starting materials for producing chemical grade hydrocarbons.

Figure 5:
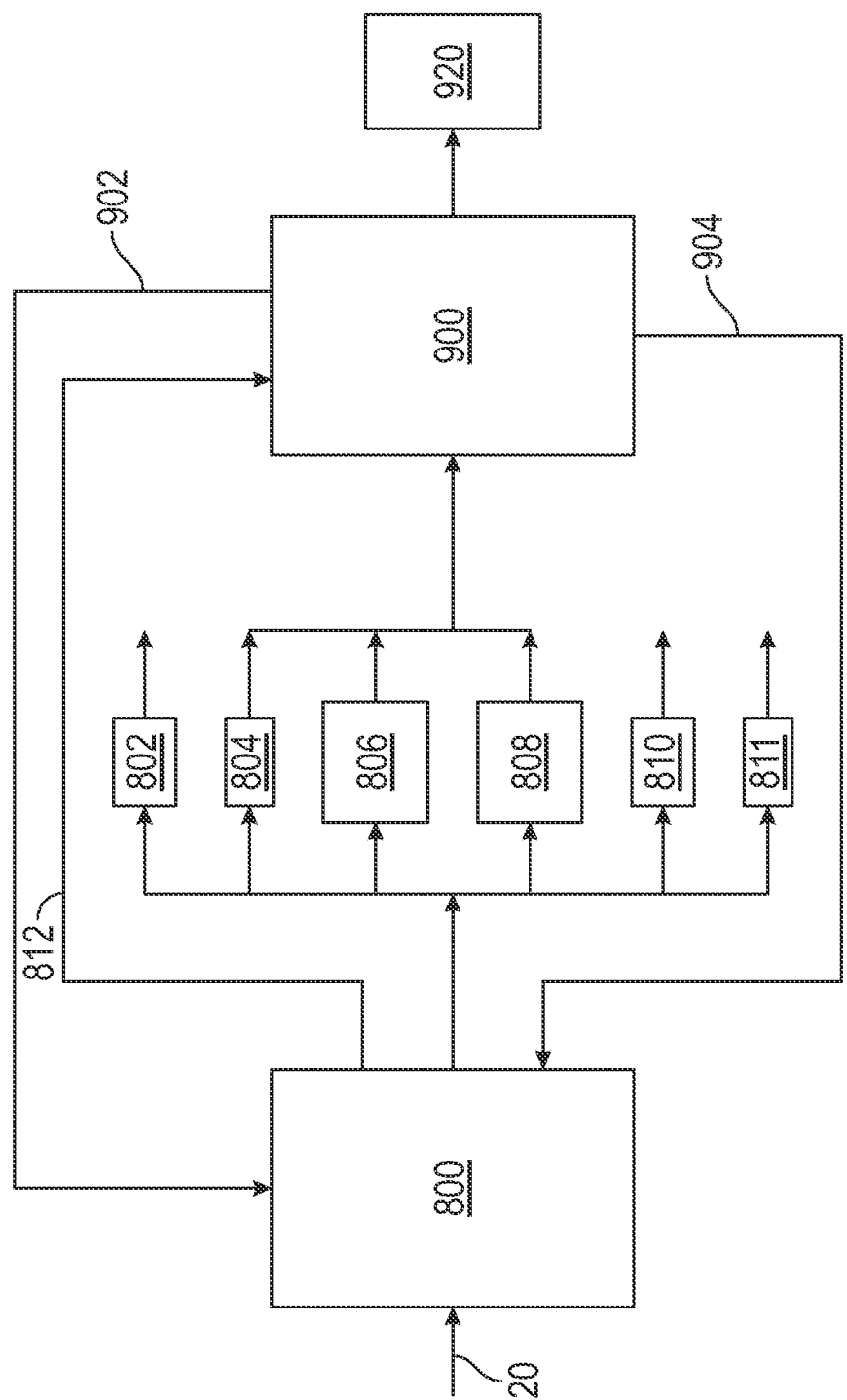
FIG. 5 is a schematic flow diagram of an integrated feed preparation unit and steam cracking unit that is one aspect of the invention.

In another broad aspect, the invention is an integrated crude processing configuration (feed preparation unit—"FPU") as described above integrated with an associated steam cracking facility (including steam cracking unit or units). The FPU and associated steam cracking unit(s) are located on a single site with common power, steam, hydrogen production, water treating facilities and the like. This aspect of the invention is illustrated in FIG. 5. Crude oil is introduced to the feed preparation facility, 800, by conduit 20. The products of the feed preparation facility (FPF) 800 include those schematically shown as 802-808, with 802 being gases; 804, ethylene and propylene; 806, naphtha; 808, gas oil; 810, coke; and 811, other products such as coke. These products, except "other" and "coke", are suitable feed streams to the steam cracking facility, 900, (particularly streams 804, 806, and 808) where chemical-grade chemicals are made. Such chemical-grade hydrocarbons include ethylene, propylene, butylenes, butadiene, benzene, toluene and xylene. Pyrolysis fuel oil, 904, is recycled to the FPF. Methane, 812, from the FPF 800 is used as fuel to heat the steam cracking unit and hydrogen made in the steam cracking unit, 902, is sent to the FPF 800.

By integrating the FPF 800 and steam cracking facility 900 the light olefins get a "free ride" in the steam cracker separation unit, methane from the FPF 900 is used for heating in the steam and $C_3$ and $C_4$ paraffins produced provide excellent feedstock for the steam cracker. The relatively small amounts of light paraffins and olefins ($C_2$-$C_3$) from the conversion FCCU 300, HCU 400, can be combined with similar products from the steam cracking unit of the steam cracking facility 900 before entering separation unit(s) downstream from the steam cracking unit of the steam cracking facility (900).

Coking process units can be blended with the products of the steam cracking unit before entering the downstream separation units of the steam cracking facility. High-purity $C_2$-$C_3$ components end up in the $C_2$- and $C_3$-product streams (basically for a "free ride") the $C_2/C_3$ paraffins are recycled back to the steam cracking unit.

Hydrogen produced in the steam cracker can supply as much as half the hydrogen need in the FPF and allows more extensive hydrotreating than would be practical in a fuel producing refinery. In some embodiments pyrolysis fuel oil produced in the steam cracker (that would otherwise be used as fuel) is recycled to the FPF to reduce the amount of crude oil feed needed.

Illustrative of the operation of the integrated system, if Arabian crude were processed and the units of the feed preparation system operated at optimum conditions and capacity the products would be approximately 6% gases, 44% naphtha, 38% gas oil, 7% coke, 2% ethylene/propylene and 3% other components. Since the liquid products would be hydrotreated, if needed, to remove sulfur compounds and other contaminants, they constitute superior steam cracking feed.

Set forth below are some examples of the process and system disclosed herein.

Embodiment 1

An integrated process comprising to convert crude oil into fractions suitable for conversion to chemicals, comprising: converting crude oil (10) in a feed preparation facility (800) by separating the crude oil to a gas fraction (101), liquid fraction (102), and first residuum fraction in an atmospheric distillation unit (100); separating the $1^{st}$ residuum to a vacuum gas oil fraction (202) and a second residuum (201) in a vacuum distillation unit (200); converting the vacuum gas oil fraction to a CU gas fraction (301,401), a CU liquid fraction (302), and an CU higher boiling fraction (303,402) in a cracking unit (300,400); and processing the second residuum fraction to DCU gas oil/lighter fraction (501) and coke (502) in a coking unit (500); and converting feedstock products from the feed preparation facility (800) into hydrocarbon products (920) in a steam cracking facility (900) by steam cracking at least one of the gas fraction (101), liquid fraction (102), CU gas fraction (301,401), and DCU gas oil/lighter fraction (501) to hydrocarbon products.

Embodiment 2

A process for preparing a feedstock for a steam cracking facility from crude oil, which process comprises: separating crude oil (10) in an atmospheric distillation unit (100) into gas (101) and liquid (102) fractions and a higher boiling first residuum fraction (103); passing the first residuum fraction (103) from the atmospheric distillation unit (100) to a vacuum distillation unit (200) where it is separated into a lighter fraction (202) and a second residuum fraction (201) and from which some of the lighter fraction (202) is optionally passed to a cracking unit (300,400); and wherein the second residuum fraction (201) from the vacuum distillation unit (200) and, optionally, heavy cycle oil (303,402) from the cracking unit (300,400) are passed to a coking unit (500) where it is processed to produce DCU gas oil/lighter fraction (501) suitable for feed to a steam cracking facility (900); wherein the gas (101) and liquid (102) fractions from the atmospheric distillation unit (100) and the lower boiling liquids (501, 401, 301, 302) from the cracking unit and coking unit, are used as feedstock for steam cracking.

Embodiment 3

The process of any of Embodiments 1-2, further comprising adding pyrolysis fuel oil (904) produced in the steam cracking facility (900) to the second residuum fraction (201).

Embodiment 4

The process of any of Embodiments 1-3, wherein the cracking unit comprises a fluid catalytic cracking unit (300).

Embodiment 5

The process of any of Embodiments 1-4, wherein the cracking unit comprises a hydrocracking cracking unit (400).

Embodiment 6

The process of any of Embodiments 1-5, further comprising hydrotreating at least one of the liquid fraction (102), CU gas fraction (401), DCU gas oil/lighter fraction (501), to remove sulfur compounds, and optionally other contaminates, e.g., to make the products more crackable in a steam cracking facility (900).

Embodiment 7

The process of any of Embodiments 1-6, wherein the conversion of the crude oil to the feedstock products is at least 75%.

Embodiment 8

The process of any of Embodiments 1-7, wherein the hydrocarbon products comprise at least one of ethylene, propylene, butylenes, butadiene, benzene, toluene, and xylene.

Embodiment 9

The process of any of Embodiments 1-8, further comprising using hydrogen (902) produced in the steam cracking facility (900) in units of the feed preparation facility (800).

Embodiment 10

The process of any of Embodiments 1-9, further comprising utilizing pyrolysis fuel oil (904) produced in the steam cracking facility (900) in units of the feed preparation facility (800).

Embodiment 11

The process of any of Embodiments 1-10, further comprising utilizing methane (812) produced in the feed preparation facility (800) in units of the steam cracking facility (900).

Embodiment 12

The process of any of Embodiments 1-11, further comprising reforming a portion of the liquid fraction (102) in a reforming unit (600) to form naphthalene (601).

Embodiment 13

The process of any of Embodiments 1-12, further comprising hydrocracking a portion of the vacuum gas oil fraction (202) to form an HCU gas fraction (401).

Embodiment 14

The process of any of Embodiments 1-13, further comprising blending light paraffins and olefins (301, 401) from the feed preparation facility (800) are blended with olefins from a steam cracking unit upstream of a separation unit, wherein the separation unit is located downstream from the steam cracking unit of the steam cracking facility (900).

Embodiment 15

The process of any of Embodiments 1-14, wherein conversion of crude oil to the feedstock products is at least 80%.

Embodiment 16

The process of any of Embodiments 1-15, wherein conversion of crude oil to the feedstock products is at least 90%.

Embodiment 17

An integrated process comprising a strategic selection of oil refining units, to convert crude oil into fractions suitable for conversion to chemicals.

Embodiment 18

An integrated process for conversion of crude oil to chemical-grade hydrocarbons including ethylene, propylene, butylenes, butadiene, benzene, toluene and xylene, comprising integrating the feed preparation process of Embodiment 17 with a steam cracking facility (900).

Embodiment 19

The integrated process of Embodiment 18, comprising passing crude oil (10) to a feed preparation facility comprising the operations of: separating crude oil (10) in an atmospheric distillation unit (100) into gas (101) and liquid (102) fractions and a higher boiling first residuum fraction (103); passing the first residuum fraction (103) from the atmospheric distillation unit (100) to a vacuum distillation unit (200) where it is separated into a lighter fraction (202) and a second residuum fraction (201) and from which some of the lighter fraction is optionally passed to a cracking unit (300,400); and wherein the second residuum fraction (201) from the vacuum distillation unit (200) and, optionally, heavy cycle oil (303,402) from the cracking unit (300,400) are passed to a coking unit (500) where it processed to produce a liquid fractions (501) suitable for feed to a steam cracking facility (900); and wherein the gas (101) and liquid (102) fractions from the atmospheric distillation unit (100), the lower boiling liquids (301,401,501) from the cracking unit (300,400) and coking unit (500), are used as feedstock for steam cracking in an associated steam cracking facility (900) and hydrogen (902) produced in steam cracking facility (900) is recycled to the (800) and methane (812) from the feed preparation facility (800) is used as fuel in the steam cracking facility (900).

Embodiment 20

The process of Embodiment 19, wherein pyrolysis gas oil (904) from the steam cracking facility (900) is recycled to the feed preparation facility 800 for feed to a coking unit (500).

Embodiment 21

The process of any of Embodiments 19-20, wherein the cracking unit (300,400) comprise a fluid catalytic unit (300), a hydrocracking unit (400), or both.

Embodiment 22

The process of any of Embodiments 1-21, wherein the atmospheric distillation unit (100), catalytic reforming unit (600), fluid catalytic cracking unit (300), vacuum distillation unit (200), and coking unit (500), are operated at typical operating conditions of temperature and pressure for such units in refinery operations.

Embodiment 23

A system for converting crude oil (10) into chemical-grade hydrocarbons (920) comprising: a feed preparation facility (800) comprising an atmospheric distillation unit (100), a vacuum distillation unit (200), a cracking unit (300,400), and a coking unit (500); and a steam cracking facility (900) for converting products from the feed preparation facility (800) into chemical-grade hydrocarbons (920); wherein the feed preparation facility (800) and the steam cracking facility (900) are physically connected with pipes and are located on the same site.

Embodiment 24

The system of Embodiment 23, further comprising a hydrogen recycle (920) from the steam cracking facility (900) to the feed preparation facility (800) and a methane line (812) from the feed preparation facility (800) to fuel the steam cracking facility (900).

Embodiment 25

The system of any of Embodiments 23-24, wherein the cracking unit at least comprises a fluid catalytic unit (300), a hydrocracking unit (400), or both.

Embodiment 26

The system of any of Embodiments 23-25, further comprising a pyrolysis fuel oil line (904) from the steam cracking facility (900) to the feed preparation facility (800).

Embodiment 27

The system of any of Embodiments 23-26, wherein light paraffins and olefin lines (301, 401) from the feed preparation facility (800) are connected to separation unit(s) downstream from the steam cracking unit of the steam cracking facility (900).

In this specification and drawings, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. An integrated process to convert crude oil into fractions suitable for conversion to chemicals, comprising:
   converting crude oil in a feed preparation facility by
      separating the crude oil to a gas fraction, liquid fraction, and first residuum fraction in an atmospheric distillation unit;
      separating the first residuum to a vacuum gas oil fraction and a second residuum fraction in a vacuum distillation unit;
      converting the vacuum gas oil fraction to a CU gas fraction, a CU liquid fraction, and an CU higher boiling fraction in a cracking unit; and
      processing the second residuum fraction to DCU gas oil/lighter fraction and coke in a coking unit; and
   directing methane, $C_3$ paraffins, $C_4$ paraffins, and feedstock products from the feed preparation facility to a steam cracking facility and converting the feedstock products into hydrocarbon products by
      steam cracking at least one of the gas fraction, liquid fraction, CU gas fraction, and DCU gas oil/lighter fraction to hydrocarbon products comprising at least one of ethylene, propylene, butylenes, butadiene, benzene, toluene, xylene, ethylbenzene, styrene, or a combination comprising at least one of the foregoing;
   using hydrogen produced in the steam cracking facility in a unit of the feed preparation facility, wherein the hydrogen produced in the steam cracking facility supplies greater than 0 to as much as half the hydrogen supplied to the feed preparation facility; and
   at least one of
      utilizing a pyrolysis fuel oil produced in the steam cracking facility in units of the feed preparation facility, and
      adding the pyrolysis fuel oil produced in the steam cracking facility to the second residuum fraction.

2. The process of claim 1, wherein the cracking unit comprises a fluid catalytic cracking unit.

3. The process of claim 1, wherein the cracking unit comprises a hydrocracking cracking unit.

4. The process of claim 1, further comprising hydrotreating at least one of the liquid fraction, CU gas fraction, DCU gas oil/lighter fraction, to remove sulfur compounds.

5. The process of claim 1, wherein the conversion of the crude oil to the feedstock products is at least 75%.

6. The process of claim 1, further comprising reforming a portion of the liquid fraction in a reforming unit to form naphthalene, benzene, toluene, and xylene.

7. The process of claim 1, further comprising hydrocracking a portion of the vacuum gas oil fraction to form an HCU gas fraction.

8. The process of claim 1, further comprising blending light paraffins and olefins from the feed preparation facility are blended with olefins from a steam cracking unit upstream of a separation unit, wherein the separation unit is located downstream from the steam cracking unit of the steam cracking facility.

9. The process of claim 1, wherein conversion of crude oil to the feedstock products is at least 80%.

10. An integrated process to convert crude oil into fractions suitable for conversion to chemicals, comprising:
    converting crude oil in a feed preparation facility by
       separating the crude oil to a gas fraction, liquid fraction, and first residuum fraction in an atmospheric distillation unit;
       separating the first residuum to a vacuum gas oil fraction and a second residuum fraction in a vacuum distillation unit;
       converting the vacuum gas oil fraction to a CU gas fraction, a CU liquid fraction, and a CU higher boiling fraction in a cracking unit; and
       processing the second residuum fraction to DCU gas oil/lighter fraction and coke in a coking unit; and converting feedstock products from the feed preparation facility into hydrocarbon products in a steam cracking facility by
   steam cracking at least one of the gas fraction, liquid fraction, CU gas fraction, and DCU gas oil/lighter fraction to hydrocarbon products comprising at least one of ethylene, propylene, butylenes, butadiene, benzene, toluene, xylene, ethylbenzene, styrene, or a combination comprising at least one of the foregoing;
using hydrogen produced in the steam cracking facility in a unit of the feed preparation facility, wherein the hydrogen produced in the steam cracking facility supplies greater than 0 to as much as half the hydrogen supplied to the feed preparation facility; and
at least one of
   utilizing a pyrolysis fuel oil produced in the steam cracking facility in units of the feed preparation facility, and
   adding the pyrolysis fuel oil produced in the steam cracking facility to the second residuum fraction;
wherein conversion of crude oil to the feedstock products is at least 90%.

11. The process of claim 1, wherein the feedstock products from the feed preparation facility comprise $C_3$ and $C_4$ paraffins.

12. The process of claim 1, wherein conversion of crude oil to the feedstock products is at least 60%.

* * * * *